(12) United States Patent
Sinha et al.

(10) Patent No.: US 8,691,861 B2
(45) Date of Patent: Apr. 8, 2014

(54) PRODRUGS OF INHIBITORS OF PLASMA KALLIKREIN

(75) Inventors: Sukanto Sinha, San Francisco, CA (US); Tamie Jo Chilcote, San Francisco, CA (US); Joghee Raju Suresh, Bangalore (IN); Sriram Narasimhan, Bangalore (IN)

(73) Assignee: ActiveSite Pharmaceuticals, Inc., San Francisco, CA (US)

(*) Notice: Subject to any disclaimer, the term of this patent is extended or adjusted under 35 U.S.C. 154(b) by 0 days.

(21) Appl. No.: 13/445,614

(22) Filed: Apr. 12, 2012

(65) Prior Publication Data

US 2012/0264798 A1    Oct. 18, 2012

Related U.S. Application Data

(60) Provisional application No. 61/517,065, filed on Apr. 13, 2011.

(51) Int. Cl.
*C07D 207/34* (2006.01)
*C07D 231/14* (2006.01)

(52) U.S. Cl.
USPC ......... 514/406; 514/423; 548/374.1; 548/537

(58) Field of Classification Search
None
See application file for complete search history.

(56) References Cited

U.S. PATENT DOCUMENTS

| | | | |
|---|---|---|---|
| 5,998,424 A | 12/1999 | Galemmo, Jr. et al. | |
| 6,337,344 B1 | 1/2002 | Defossa et al. | |
| 7,144,902 B1 | 12/2006 | Baucke et al. | |
| 7,625,944 B2 | 12/2009 | Sinha et al. | |
| 7,977,380 B2 | 7/2011 | Sinha et al. | |
| 2005/0282805 A1 | 12/2005 | Hangeland et al. | |

FOREIGN PATENT DOCUMENTS

| | | |
|---|---|---|
| JP | 2001-527066 A | 12/2001 |
| JP | 2002-507968 A | 3/2002 |
| WO | 99/28297 A1 | 6/1999 |
| WO | 00/61609 A2 | 10/2000 |
| WO | 02/14270 A1 | 2/2002 |
| WO | 2006/027135 A1 | 3/2006 |
| WO | 2008/016883 A2 | 2/2008 |
| WO | 2009/097141 A1 | 8/2009 |
| WO | 2011/075684 A1 | 6/2011 |

OTHER PUBLICATIONS

Govers-Riemslag et al., Journal of Thromosis and Haemostasis, 2007, 5, 1896-903.
Phipps et al., Kidney International, 2008, 73, 1114-9.
Phipps et al., Hypertension, 2009, vol. 53, pp. 175-181.
Schmaier, J. Clin. Invest., 2002, 109, 1007-9.
Koshio et al, "Orally active factor Xa inhibitor: synthesis and biological activity of masked amidines as prodrugs of novel 1,4-diazepane derivatives," Bioorganic and Medicinal Chemistry, 2004, vol. 12, pp. 5415-5426.
Uchida et al., "Orally active factor Xa inhibitors. Investigation of a novel series of 3-amidinophenyl sulfonamide derivatives using an amidoxime prodrug strategy," Bioorganic and Medicinal Chemistry Letters, 2008, vol. 18, pp. 4682-4687.
Weller et al., "Orally Active Fibrinogen Receptor Antagonists. 2. Amidoximes as Prodrugs of Amidines," Journal of Medicinal Chemistry, 1996, vol. 39, pp. 3139-3147.
International Search Report and Written Opinion, Aug. 14, 2012, PCT application No. PCT/US2012/033353, 9 pages.

*Primary Examiner* — Kamal Saeed
(74) *Attorney, Agent, or Firm* — Kilpatrick Townsend & Stockton LLP; William B. Kezer

(57) ABSTRACT

This invention provides new pharmaceutically useful compounds that are prodrugs of inhibitors of plasma kallikrein and methods and compositions for preventing or treating plasma kallikrein dependent diseases or conditions, such as diabetic macular edema or hemorrhagic stroke, by administering prodrugs of the formula:

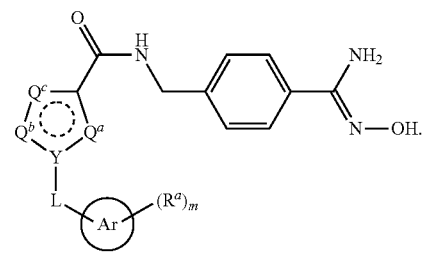

31 Claims, 1 Drawing Sheet

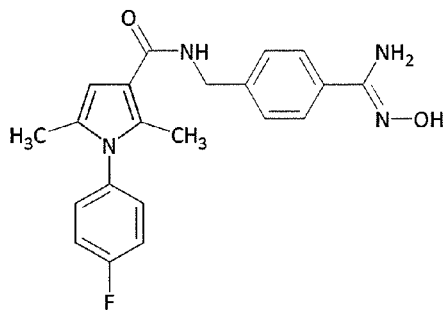
1-(4-fluorophenyl)-*N*-(4-(*N*'-hydroxycarbamimidoyl)
benzyl)-2,5-dimethyl-1*H*-pyrrole-3-carboxamide
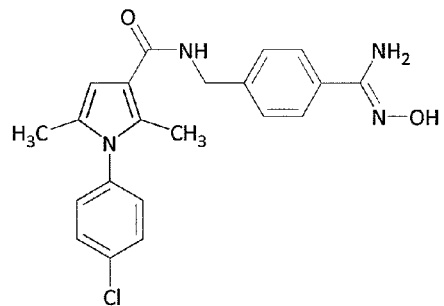
1-(4-chlorophenyl)-*N*-(4-(*N*'-hydroxycarbamimidoyl)
benzyl)-2,5-dimethyl-1*H*-pyrrole-3-carboxamide
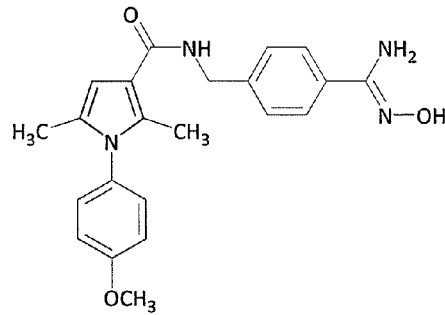
1-(4-methoxyphenyl)-*N*-(4-(*N*'-hydroxycarbamimidoyl)
benzyl)-2,5-dimethyl-1*H*-pyrrole-3-carboxamide
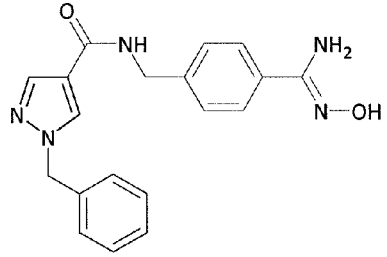
1-benzyl-*N*-(4-(*N*'-hydroxycarbamimidoyl)benzyl)-1*H*-
pyrazole-4-carboxamide

PRODRUGS OF INHIBITORS OF PLASMA KALLIKREIN

CROSS-REFERENCES TO RELATED APPLICATIONS

This application claims the benefit of U.S. Ser. No. 61/517,065, filed Apr. 13, 2011, the contents of which are incorporated herein by reference.

STATEMENT AS TO RIGHTS TO INVENTIONS MADE UNDER FEDERALLY SPONSORED RESEARCH OR DEVELOPMENT

This invention was made with United States Government support under grant EY019629 awarded by the National Institutes of Health to ActiveSite Pharmaceuticals, Inc. The Government has certain rights to this invention.

REFERENCE TO A "SEQUENCE LISTING," A TABLE, OR A COMPUTER PROGRAM LISTING APPENDIX SUBMITTED ON A COMPACT DISK

NOT APPLICABLE

BACKGROUND OF THE INVENTION

Plasma kallikrein (PK), a serine protease present in plasma as the inactive zymogen precursor plasma prekallikrein (prePK), is proteolytically activated by FXIIa. In a positive feedback loop, PK proteloytically activates the zymogen FXII, leading to additional FXIIa formation, further amplifying its own activation. FXIIa also activates the zymogen FXI to active FXIa, which results in the initiation of the intrinsic (contact) pathway of blood coagulation, resulting in generation of thrombin, and cleavage of fibrinogen. Importantly, PK cleaves high molecular weight kininogen (HMWK) to generate bradykinin. Bradykinin is able to open the tight junctions between endothelial cells lining blood vessels by activating its receptors, B1 and B2, present on the endothelial cells' surface, and thus allowing fluid and plasma protein to extravasate into tissue, a condition known as increased vascular permeability. Disruption of tight junctions of the blood-brain barrier, and consequent leakage of plasma and proteins into the brain (edema) have also been associated with neurodegenerative diseases, such as Alzheimer's Disease, Parkinson's Disease, and multiple sclerosis (MS), as well as with CNS infections and brain tumors. For example, peritumoral brain edema results in poorer prognosis in patients with glioblastoma multiforme (Schoenegger K, Oberndorfer S, *Eur J Neurol.* 2009 July; 16(7):874-8). The increased vascular permeability caused by bradykinin formation can result in the accumulation of excess fluid (edema) in many tissues and organs in various diseases, e.g., angioedema, cystoid macular edema, diabetic macular edema, macular edema after retinal vein occlusion, cerebrovascular edema following stroke or head trauma, and capillary leak syndrome. For example, the PK inhibitor ASP-440 (known from WO 2008/016883, and U.S. Pat. No. 7,625,944) has been shown to reduce angiotensin-II-induced retinal vascular permeability, and elevated systolic blood pressure (Phipps, J. A., et al. (2009) *Hypertension* 53: 175-181). Elevated levels of PK in the eyes of rodents results in increased fluorescein leakage, and retinal edema, and ASP-440 inhibits plasma leakage into the retina in diabetic animals (Clermont A. C., et al. (2011) *Diabetes,* 60: 1590-8). Activation of prePK and the contact system has also been shown to cause anaphylaxis, e.g., in patients treated with contaminated heparin (Kishimoto, T. K., et al. (2008) *N. Engl. J. Med.* 358: 2457-2467).

Despite the developing body of knowledge surrounding plasma kallikrein-related diseases, there remains a need for the development of new therapeutic agents that are useful in the treatment of those diseases. Surprisingly, the present invention provides such compounds.

BRIEF SUMMARY OF THE INVENTION

In one aspect, the present invention provides a new compound having the formula:

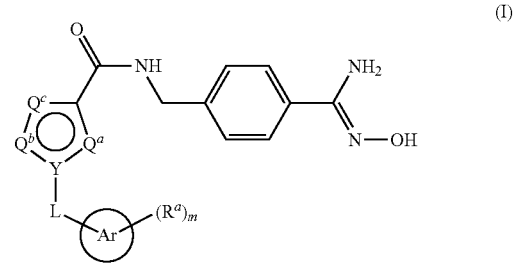

(I)

wherein Ar is an aromatic ring selected from the group consisting of benzene, pyridine and pyrimidine; the subscript m is an integer of from 0 to 5; each $R^a$ is independently selected from the group consisting of cycloalkyl, haloalkyl, halogen, —OH, —OR$^1$, —OSi(R$^1$)$_3$, —OC(O)O—R$^1$, —OC(O)R$^1$, —(O)NHR$^1$, —OC(O)N(R$^1$)$_2$, —SH, —SR$^1$, —S(O)R$^1$, —S(O)$_2$R$^1$, —SO$_2$NH$_2$, —S(O)$_2$NHR$^1$, —S(O)$_2$N(R$^1$)$_2$, —NHS(O)$_2$R$^1$, —NR$^1$S(O)$_2$R$^1$, —C(O)NH$_2$, —C(O)NHR$^1$, —C(O)N(R$^1$)$_2$, —C(O)R$^1$, —C(O)H, —C(=S)R$^1$, —NHC(O)R$^1$, —NR$^1$C(O)R$^1$, —NHC(O)NH$_2$, —NR$^1$C(O)NH$_2$, —NR$^1$C(O)NHR$^1$, —NHC(O)NHR$^1$, —NR$^1$C(O)N(R$^1$)$_2$, —NHC(O)N(R$^1$)$_2$, —CO$_2$H, —CO$_2$R$^1$, —NHCO$_2$R$^1$, —NR$^1$CO$_2$R$^1$, —R$^1$, —CN, —NO$_2$, —NH$_2$, —NHR$^1$, —N(R$^1$)$_2$, —NR$^1$S(O)NH$_2$, —NR$^1$S(O)$_2$NHR$^1$, —NH$_2$C(=NR$^1$)NH$_2$, —N=C(NH$_2$)NH$_2$, —C(=NR$^1$)NH$_2$, —NH—OH, —NR$^1$—OH, —NR$^1$—OR$^1$, —N=C=O, —N=C=S, —Si(R$^1$)$_3$, —NH—NHR$^1$, —NHC(O)NHNH$_2$, NO, —N=C=NR$^1$ and —SCN, wherein each R$^1$ is independently C$_{1-8}$ alkyl; L is a linking group selected from the group consisting of a bond, CH$_2$ and SO$_2$;

Q$^a$, Q$^b$, and Q$^c$ are each members independently selected from the group consisting of N, S, O and C(R$^q$) wherein each R$^q$ is independently selected from the group consisting of H, C$_{1-8}$ alkyl and phenyl, and the ring having Q$^a$, Q$^b$, Q$^c$ and Y as ring vertices is a five-membered ring having two double bonds; Y is a member selected from the group consisting of C and N;

The compounds of general formula I are prodrugs of the plasma kallikrein inhibitor compounds of general formula II, which are already known from WO 2008/016883, and U.S. Pat. No. 7,625,944. Approaches to synthesize prodrugs of compounds that contain amidine moieties are known in the art. However, compounds of general formula I have never been previously described or taught by the prior art, nor have their particular advantages as PK inhibitors in vivo been described. Upon administration to a subject in need of treatment with a plasma kallikrein inhibitor, the compounds provided herein are converted in vivo into compounds of general formula II, and therefore have valuable properties as pharmaceutical agents.

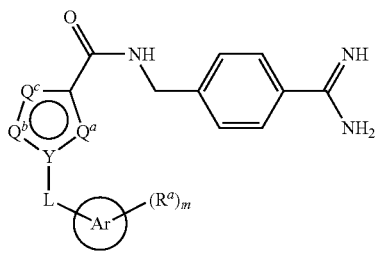

(II)

The symbols $Q_a$, $Q_b$, $Q_c$, Y, L, Ar, $R^a$ and m in general formula II have the same meaning as in general formula I.

The following are mentioned as examples of particularly preferred compounds of general formula I:
(a) 1-(4-fluorophenyl)-N-[[4-(N'-hydroxycarbamimidoyl)phenyl]methyl]-2,5-dimethyl-pyrrole-3-carboxamide;
(b) 1-(4-chlorophenyl)-N-[[4-(N'-hydroxycarbamimidoyl)phenyl]methyl]-2,5-dimethyl-pyrrole-3-carboxamide;
(c) 1-(4-methoxyphenyl)-N-[[4-(N'-hydroxycarbamimidoyl)phenyl]methyl]-2,5-dimethyl-pyrrole-3-carboxamide
(d) 1-benzyl-N-[[4-(N'-hydroxycarbamimidoyl)phenyl]methyl]pyrazole-4-carboxamide.
(e) N-[[4-(N'-hydroxycarbamimidoyl)phenyl]methyl]-2,5-dimethyl-1-(4-pyridylmethyl)pyrrole-3-carboxamide In another aspect, the present invention provides compounds having the formula:

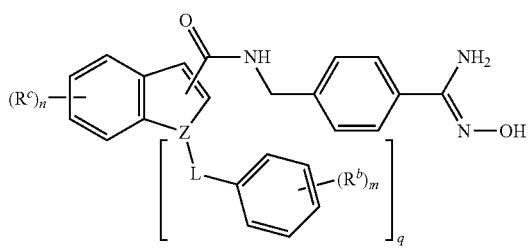

(III)

wherein the subscript m is an integer of from 0 to 5; the subscript n is an integer of from 0 to 4; the subscript q is an integer of from 0 to 1; L is a linking group selected from the group consisting of a bond, $CH_2$ and $SO_2$; each of $R^b$ and $R^c$ is independently selected from the group consisting of cycloalkyl, haloalkyl, halogen, —OH, —$OR^2$, —$OSi(R^2)_3$, —OC(O)O—$R^2$, —OC(O)$R^2$, —OC(O)$NHR^2$, —OC(O)N$(R^2)_2$, —SH, —$SR^2$, —S(O)$R^2$, —S(O)$_2R^2$, —$SO_2NH_2$, —S(O)$_2NHR^2$, —S(O)$_2N(R_2)_2$, —NHS(O)$_2R^2$, —$NR^2$S(O)$_2R^2$, —C(O)$NH_2$, —C(O)$NHR^2$, —C(O)N$(R^2)_2$, —C(O)$R^2$, —C(O)H, —C(=S)$R^2$, —NHC(O)$R^2$, —$NR^2$C(O)$R^2$, —NHC(O)$NH_2$, —$NR^2$C(O)$NH_2$, —$NR^2$C(O)$NHR^2$, —NHC(O)$NHR^2$, —$NR^2$C(O)N$(R^2)_2$, —NHC(O)N$(R^2)_2$, —$CO_2H$, —$CO_2R^2$, —$NHCO_2R^2$, —$NR^2CO_2R^2$, —$R^2$, —CN, —$NO_2$, —$NH_2$, —$NHR^2$, —N$(R^2)_2$, —$NR^2$S(O)$NH_2$, —$NR^2$S(O)$_2NHR^2$, —$NH_2$C(=$NR^2$)$NH_2$, —N=C($NH_2$)$NH_2$, —C(=$NR^2$)$NH_2$, —NH—OH, —$NR^2$—OH, —$NR^2$—$OR^2$, —N=C=O, —N=C=S, —Si$(R^2)_3$, —NH—$NHR^2$, —NHC(O)$NHNH_2$, NO, —N=C=$NR^2$ and —S—CN, wherein each $R^2$ is independently $C_{1-8}$ alkyl; when q is 0, Z is a member selected from the group consisting of O, S and $NR^d$ wherein $R^d$ is H or $C_1$-$C_8$ alkyl; when q is 1, Z is N;

The compounds of general formula III are prodrugs of the plasma kallikrein inhibitor compounds of general formula IV (the parent compounds are described in WO 2008/016883, and U.S. Pat. No. 7,625,944). However, compounds of general formula III have not been previously described. Upon administration to a subject in need of treatment with a plasma kallikrein inhibitor, the compounds of formula III are converted in vivo into compounds of general formula IV, and therefore have valuable properties as pharmaceutical agents.

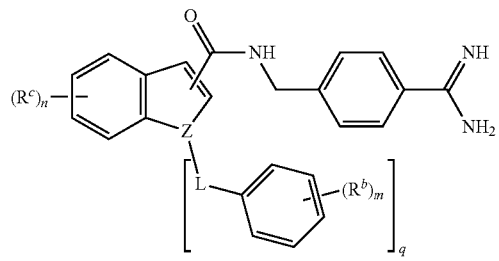

(IV)

Here, the symbols $R^b$, $R^c$, L, Z, m, n and q in general formula IV have the same meaning as in general formula III.

The following are mentioned as examples of particularly preferred compounds of general formula III:
(a) 1-benzyl-N-[[4-(N'-hydroxycarbamimidoyl)phenyl]methyl]indole-3-carboxamide;
(b) 1-(benzenesulfonyl)-N-[[4-(N'-hydroxycarbamimidoyl)phenyl]methyl]indole-3-carboxamide.

In yet another aspect, the present invention provides a pharmaceutical composition. The composition includes a compound of formula I or III, in combination with a pharmaceutically acceptable excipient.

In a further aspect, the present invention provides a method of treating conditions associated with diabetes and hypertension, e.g., retinopathy, macular edema, nephropathy, neuropathy and elevated blood pressure.

In another aspect, the present invention provides a method of treating a clinical condition that is caused by or is aggravated by excessive vascular permeability and consequent edema, e.g., ischemic and hemorrhagic stroke, diabetic macular edema, cystoid macular edema, retinal vein occlusions, age-related macular degeneration, head trauma, capillary leak syndrome, and glioblastoma multiforme.

In still another aspect, the present invention provides a method of treating a plasma kallikrein-related disorder or condition in a subject in need thereof. The method includes administering to the subject a compound of formula I or III.

BRIEF DESCRIPTION OF THE DRAWINGS

FIG. 1 provides structures of selected compounds of the invention.

DETAILED DESCRIPTION OF THE INVENTION

I. Definitions

Unless otherwise stated the following terms used in the specification and claims have the meanings given below.

The term "alkyl", by itself or as part of another substituent, means, unless otherwise stated, a straight or branched chain hydrocarbon radical, having the number of carbon atoms designated (i.e. $C_{1-8}$ means one to eight carbons). Examples of alkyl groups include methyl, ethyl, n-propyl, isopropyl, n-butyl, t-butyl, isobutyl, sec-butyl, n-pentyl, n-hexyl, n-heptyl, n-octyl, and the like. For each of the definitions herein (e.g., alkyl, alkoxy, alkylamino, alkylthio, alkylene, haloalkyl), when a prefix is not included to indicate the number of main chain carbon atoms in an alkyl portion, the radical or portion thereof will have 12 or fewer main chain carbon atoms.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having four or fewer carbon atoms.

The term "cycloalkyl" refers to hydrocarbon rings having the indicated number of ring atoms (e.g., $C_{3-6}$cycloalkyl) and being fully saturated or having no more than one double bond between ring vertices. One or two C atoms may optionally be replaced by a carbonyl. "Cycloalkyl" is also meant to refer to bicyclic and polycyclic hydrocarbon rings such as, for example, bicyclo[2.2.1]heptane, bicyclo[2.2.2]octane, etc. When a prefix is not included to indicate the number of ring carbon atoms in a cycloalkyl, the radical or portion thereof will have 8 or fewer ring carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "$C_{1-4}$ haloalkyl" is mean to include trifluoromethyl, 2,2,2-trifluoroethyl, 4-chlorobutyl, 3-bromopropyl, and the like.

The term "aryl" means a monovalent monocyclic, bicyclic or polycyclic aromatic hydrocarbon radical of 5 to 14 ring atoms which is unsubstituted or substituted independently with one to four substituents, preferably one, two, or three substituents selected from alkyl, cycloalkyl, cycloalkyl-alkyl, halo, cyano, hydroxy, alkoxy, amino, acylamino, mono-alkylamino, di-alkylamino, haloalkyl, haloalkoxy, heteroalkyl, COR (where R is hydrogen, alkyl, cycloalkyl, cycloalkylalkyl cut, phenyl or phenylalkyl, aryl or arylalkyl), —$(CR'R'')_n$—COOR (where n is an integer from 0 to 5, R' and R" are independently hydrogen or alkyl, and R is hydrogen, alkyl, cycloalkyl, cycloalkylalkyl cut, phenyl or phenylalkyl aryl or arylalkyl) or —$(CR'R'')_n$—$CONR^aR^b$ (where n is an integer from 0 to 5, R' and R" are independently hydrogen or alkyl, and $R^a$ and $R^b$ are, independently of each other, hydrogen, alkyl, cycloalkyl, cycloalkylalkyl, phenyl or phenylalkyl, aryl or arylalkyl). More specifically the term aryl includes, but is not limited to, phenyl, biphenyl, 1-naphthyl, and 2-naphthyl, and the substituted forms thereof. Similarly, the term "heteroaryl" refers to those aryl groups wherein one to five heteroatoms or heteroatom functional groups have replaced a ring carbon, while retaining aromatic properties, e.g., pyridyl, quinolinyl, quinazolinyl, thienyl, and the like. The heteroatoms are selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl groups include phenyl, naphthyl and biphenyl, while non-limiting examples of heteroaryl groups include pyridyl, pyridazinyl, pyrazinyl, pyrimindinyl, triazinyl, quinolinyl, quinoxalinyl, quinazolinyl, cinnolinyl, phthalaziniyl, benzotriazinyl, purinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzofuranyl, benzothienyl, indolyl, quinolyl, isoquinolyl, isothiazolyl, pyrazolyl, indazolyl, pteridinyl, imidazolyl, triazolyl, tetrazolyl, oxazolyl, isoxazolyl, thiadiazolyl, pyrrolyl, thiazolyl, furyl, thienyl and the like. For brevity, the term aryl, when used in combination with other radicals (e.g., aryloxy, arylalkyl) is meant to include both aryl groups and heteroaryl groups as described above.

Substituents for the aryl groups are varied and are generally selected from: -halogen, —OR', —OC(O)R', —NR'R", —SR', —R', —CN, —$NO_2$, —$CO_2R'$, —CONR'R", —C(O)R', —OC(O)NR'R", —NR"C(O)R', —NR"C(O)$_2$R', —NR'—C(O)NR"R''', —NH—C(NH$_2$)=NH, —NR'C(NH$_2$)=NH, —NH—C(NH$_2$)=NR', —S(O)R', —S(O)$_2$R', —S(O)$_2$NR'R", —NR'S(O)$_2$R", —$N_3$, perfluoro($C_1$-$C_4$)alkoxy, and perfluoro($C_1$-$C_4$)alkyl, in a number ranging from zero to the total number of open valences on the aromatic ring system; and where R', R" and R''' are independently selected from hydrogen, $C_{1-8}$ alkyl, $C_{3-6}$ cycloalkyl, $C_{2-8}$ alkenyl, $C_{2-8}$ alkynyl, unsubstituted aryl and heteroaryl, (unsubstituted aryl)-$C_{1-4}$ alkyl, and unsubstituted aryloxy-$C_{1-4}$ alkyl.

Two of the substituents on adjacent atoms of the aryl or heteroaryl ring may optionally be replaced with a substituent of the formula -T-C(O)—$(CH_2)_q$—U—, wherein T and U are independently —NH—, —O—, —$CH_2$— or a single bond, and q is an integer of from 0 to 2. Alternatively, two of the substituents on adjacent atoms of the aryl or heteroaryl ring may optionally be replaced with a substituent of the formula -A-$(CH_2)_r$—B—, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —$(CH_2)_s$—W—$(CH_2)_t$—, where s and t are independently integers of from 0 to 3, and W is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted $C_{1-6}$ alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occuring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperadine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts. The term "pharmaceutically acceptable" is meant the carrier, diluent or excipient must be compatible with the other ingredients of the formulation and not deleterious to the recipient thereof.

The term "composition" as used herein is intended to encompass a product comprising the specified ingredients in the specified amounts, as well as any product which results, directly or indirectly, from combination of the specified ingredients in the specified amounts.

The term "subject" as used herein is meant to include animals, such as mammals, including, but are not limited to, primates (e.g. humans), cows, sheep, goats, horses, dogs, cats, rabbits, rats, mice and the like.

II. General

The present invention relates to compounds and methods of using the compounds and pharmaceutical compositions for the prevention and treatment of plasma kallikrein-dependent diseases or conditions. The diseases or conditions that can be treated using the compounds of the present invention include, but are not limited to, ischemic stroke, hemorrhagic stroke, hypertension and its vascular complications (especially retinopathy and nephropathy), cerebrovascular edema, pulmonary hypertension, inflammation, pain, acute myocardial infarction (MI), deep vein thrombosis (DVT), complications from fibrinolytic treatment (e.g., with tissue plasminogen activator, streptokinase) following stroke or MI, angina, angioedema, sepsis, arthritis, complications of cardiopulmonary bypass, capillary leak syndrome, inflammatory bowel disease, diabetes and its vascular complications (especially retinopathy, diabetic macular edema, nephropathy and neuropathy), age-related macular degeneration, retinal vein occlusions, brain edema, ischemia-reperfusion injury, angiogenesis (e.g., in cancer), asthma, anaphylaxis, and cerebrovascular complications of neurological conditions (e.g., Alzheimer's Disease, Parkinson's Disease, multiple sclerosis, CNS infections, and glioblastoma multiforme).

III. Compounds

In one aspect, the present invention provides compounds having the formula:

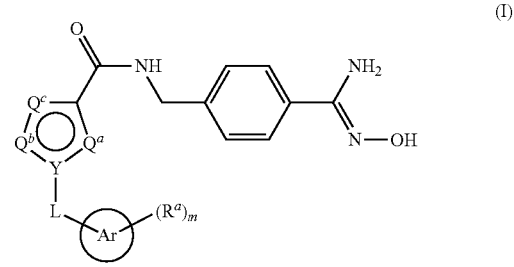

Ar is an aromatic ring selected from the group consisting of benzene, pyridine and pyrimidine. In one embodiment, Ar is benzene or pyridine. The subscript m is an integer from 0 to 5. In one embodiment, m is 0.

Each $R^a$ is independently selected from the group consisting of cycloalkyl, haloalkyl, halogen, —OH, —OR$^1$, —OSi(R$^1$)$_3$, —OC(O)O—R$^1$, —OC(O)R$^1$, —OC(O)NHR$^1$, —OC(O)N(R$^1$)$_2$, —SH, —SR$^1$, —S(O)R$^1$, —S(O)$_2$R$^1$, —SO$_2$NH$_2$, —S(O)$_2$NHR$^1$, —S(O)$_2$N(R$^1$)$_2$, —NHS(O)$_2$R$^1$, —NR$^1$S(O)$_2$R$^1$, —C(O)NH$_2$, —C(O)NHR$^1$, —C(O)N(R$^1$)$_2$, —C(O)R$^1$, —C(O)H, —C(=S)R$^1$, —NHC(O)R$^1$, —NR$^1$C(O)R$^1$, —NHC(O)NH$_2$, —NR$^1$C(O)NH$_2$, —NR$^1$C(O)NHR$^1$, —NHC(O)NHR$^1$, —NR$^1$C(O)NR$^1$)$_2$, —NHC(O)N(R$^1$)$_2$, —CO$_2$H, —CO$_2$R$^1$, —NHCO$_2$R$^1$, —NR$^1$CO$_2$R$^1$, —R$^1$, —CN, —NO$_2$, —NH$_2$, —NHR$^1$, —N(R$^1$)$_2$, —NR$^1$S(O)NH$_2$, —NR$^1$S(O)$_2$NHR$^1$, —NH$_2$C(=NR$^1$)NH$_2$, —N=C(NH$_2$)NH$_2$, —C(=NR$^1$)NH$_2$, —NH—OH, —NR$^1$—OH, —NR$^1$—OR$^1$, —N=C=O, —N=C=S, —Si(R$^1$)$_3$, —NH—NHR$^1$, —NHC(O)NHNH$_2$, NO, —N=C=NR$^1$ and —S—CN, wherein each $R^1$ is independently alkyl. In one embodiment, $R^1$ is $C_1$-$C_8$ alkyl. In another embodiment, $R^1$ is unsubstituted aryl, such as phenyl or pyridyl, or a substituted aryl, such as a substituted phenyl or a substituted pyridyl.

In one embodiment, each $R^a$ is independently selected from the group consisting of $C_1$-$C_8$ alkyl, $C_1$-$C_8$ alkoxy, aryl, aryl($C_1$-$C_8$ alkyl), halogen, —$NH_2$, —NH($C_1$-$C_8$ alkyl), —N($C_1$-$C_8$ alkyl)$_2$, —CN, —C(=O)($C_1$-$C_8$ alkyl), —C(=O)$NH_2$, —C(=O)NH($C_1$-$C_8$ alkyl), —C(=O)N($C_1$-$C_8$ alkyl)$_2$, —OH, —COOH, —COO($C_1$-$C_8$ alkyl), —OCO ($C_1$-$C_8$ alkyl), —O(C=O)O($C_1$-$C_8$ alkyl)—$NO_2$, —SH, —S($C_1$-$C_8$ alkyl), —NH(C=O)($C_1$-$C_8$ alkyl), —NH(C=O)O($C_1$-$C_8$ alkyl), —O(C=O)NH($C_1$-$C_8$ alkyl), —$SO_2$($C_1$-$C_8$ alkyl), —$NHSO_2$($C_1$-$C_8$ alkyl) and —$SO_2NH$($C_1$-$C_8$ alkyl). In another embodiment, each $R^a$ is independently selected from the group consisting of $C_1$-$C_8$ alkyl, $C_1$-$C_8$ alkoxy, phenyl, phenyl($C_1$-$C_8$ alkyl), halogen, —CN, —$NH_2$, —NH($C_1$-$C_8$ alkyl), —N($C_1$-$C_8$ alkyl)$_2$, —(C=O)$CH_3$, —(C=O)$NH_2$, —OH, —COOH, —COO($C_1$-$C_8$ alkyl), —OCO($C_1$-$C_8$ alkyl), —O(C=O)O($C_1$-$C_8$ alkyl), —$NO_2$, —SH, —S($C_1$-$C_8$ alkyl), and —NH(C=O)($C_1$-$C_8$ alkyl). In yet another embodiment, each $R^a$ is independently selected from the group consisting of $C_1$-$C_8$ alkyl, $C_1$-$C_8$ alkoxy, phenyl, phenyl ($C_1$-$C_8$ alkyl), phenoxy, aryloxy, halogen, —CN, —$NH_2$, —NH-aryl, —(C=O)$CH_3$, —(C=O)$NH_2$, —OH, —COOH, —COO($C_1$-$C_8$ alkyl), —OCO($C_1$-$C_8$ alkyl), —COO-aryl, —OC(O)-aryl, —O(C=O)O($C_1$-$C_8$ alkyl)—$NO_2$, —SH, —S($C_1$-$C_8$ alkyl), —NH(C=O)($C_1$-$C_8$ alkyl) and the like. For example, $R^a$ is halogen, such as Cl, Br or I.

L is a linking group selected from the group consisting of a bond, $CH_2$ and $SO_2$.

The ring vertex labeled Y is C or N. The vertices labeled $Q^a$, $Q^b$, and $Q^c$ are each members independently selected from the group consisting of N, S, O and C($R^q$) wherein each $R^q$ is independently selected from the group consisting of H, $C_{1-8}$ alkyl, halogen and phenyl, and the ring having $Q^a$, $Q^b$, $Q^c$ and Y as ring vertices is a five-membered ring having two double bonds.

In a first group of embodiments, $Q^a$ is N and $Q^b$ and $Q^c$ are each selected from N, O and C($R^q$). In certain instances, $Q^a$ is N and $Q^c$ and $Q^b$ are each independently selected from N and C($R^q$). In certain other instances, $Q^a$ is N and $Q^c$ and $Q^b$ are each selected from C($R^q$) and O. In yet certain other instances, $Q^a$ is N, $Q^c$ is a member selected from N and O, and $Q^b$ is the other member selected from N and O.

In a second group of embodiments, $Q^a$ is O and $Q^b$ and $Q^c$ are each selected from N, O and C($R^q$). In certain instances, $Q^a$ is O and $Q^c$ and $Q^b$ are each independently selected from N and C($R^q$).

In a third group of embodiments, $Q^a$ is C($R^q$) and $Q^b$ and $Q^c$ are each selected from N, O and C($R^q$). In certain instances, $Q^a$ is C($R^q$) and $Q^b$ and $Q^c$ are each independently selected from N and O. In certain other instances, $Q^a$ is C($R^q$) and $Q^b$ and $Q^c$ are each independently selected from N and C($R^q$). In yet certain other instances, $Q^a$ is C($R^q$) and $Q^b$ and $Q^c$ are each independently selected from O and C($R^q$). In one occurrence, $Q^a$ is C($R^q$), $Q^b$ is O and $Q^c$ is (C$R^q$).

In one embodiment, Y is C, $Q^a$ is S and Ar is selected from phenyl or pyridyl. In another embodiment, Y is N, $Q^a$, $Q^b$ and $Q^c$ are each independently C($R^q$), wherein $R^q$ is H or $C_{1-8}$alkyl. In one instance, Y is N, $Q^a$ and $Q^c$ are C($R^q$) and $Q^b$ is CH. In a preferred embodiment, Y is N.

In one embodiment, L is a bond, Y is N. In another embodiment, L is a bond, Y is N and Ar is a benzene ring. In yet another embodiment, L is $CH_2$ and Y is N. In still another embodiment, L is a bond and Y is C. In a further embodiment, L is $SO_2$ and Y is N.

In a preferred embodiment, $Q^a$, $Q^b$ and $Q^c$ are each independently $CR^q$. In another preferred embodiment, L is a bond or $CH_2$. In still another preferred embodiment, Ar is benzene. In still another preferred embodiment, $R^a$ is —H and $C_1$-$C_8$ alkyl.

In another embodiment, the compounds of formula I have a subformula Ia:

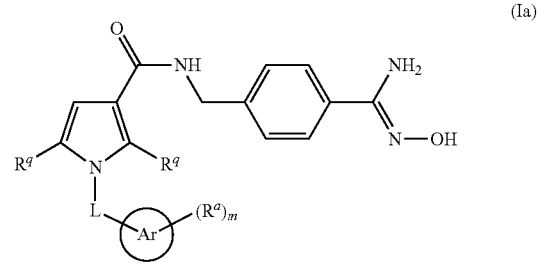

wherein $R^q$ and L are as defined above. In one instance, each $R^q$ is independently —H or $C_{1-8}$ alkyl and L is a bond or —$CH_2$—. In another instance, L is a bond and $R^a$ is a halogen. For example, $R^a$ is —Cl, —F.

In one embodiment, the compounds of formula I have a subformula Ib:

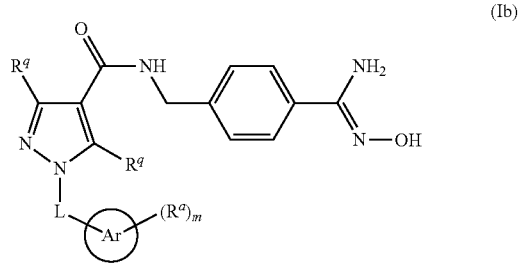

wherein Ar is an aromatic ring. In one instance, each $R^q$ is independently H, $C_{1-8}$ alkyl or halogen. In another instance, L is a bond or $CH_2$. In yet another instance, Ar is benzene. In still another instance, m is 0. In one occurrence, each $R^q$ is H, L is $CH_2$, Ar is benzene and m is 0. In another occurrence, each $R^q$ is H, L is a bond, Ar is benzene and m is 0.

The following are mentioned as examples of particularly preferred compounds of general formula I:

(a) 1-(4-fluorophenyl)-N-[[4-(N'-hydroxycarbamimidoyl)phenyl]methyl]-2,5-dimethyl-pyrrole-3-carboxamide;

(b) 1-(4-chlorophenyl)-N-[[4-(N'-hydroxycarbamimidoyl)phenyl]methyl]-2,5-dimethyl-pyrrole-3-carboxamide;

(c) 1-(4-methoxyphenyl)-N-[[4-(N'-hydroxycarbamimidoyl)phenyl]methyl]-2,5-dimethyl-pyrrole-3-carboxamide;

(d) 1-benzyl-N-[[4-(N'-hydroxycarbamimidoyl)phenyl]methyl]pyrazole-4-carboxamide;

(e) N-[[4-(N'-hydroxycarbamimidoyl)phenyl]methyl]-2,5-dimethyl-1-(4-pyridylmethyl)pyrrole-3-carboxamide.

Preparation of Compounds

Many methods of synthesizing the compounds of the present invention are known in the art. One preferred method for synthesizing compounds of general formula I is illustrated graphically below, where 1 equivalent of the corresponding carboxylic acid is reacted with 1 equivalent of 4-(aminomethyl)benzonitrile in the presence of 1.1 equivalents of oxalyl chloride, 3 equivalents of triethylamine in dichloromethane at room temperature for 3 h (step a).

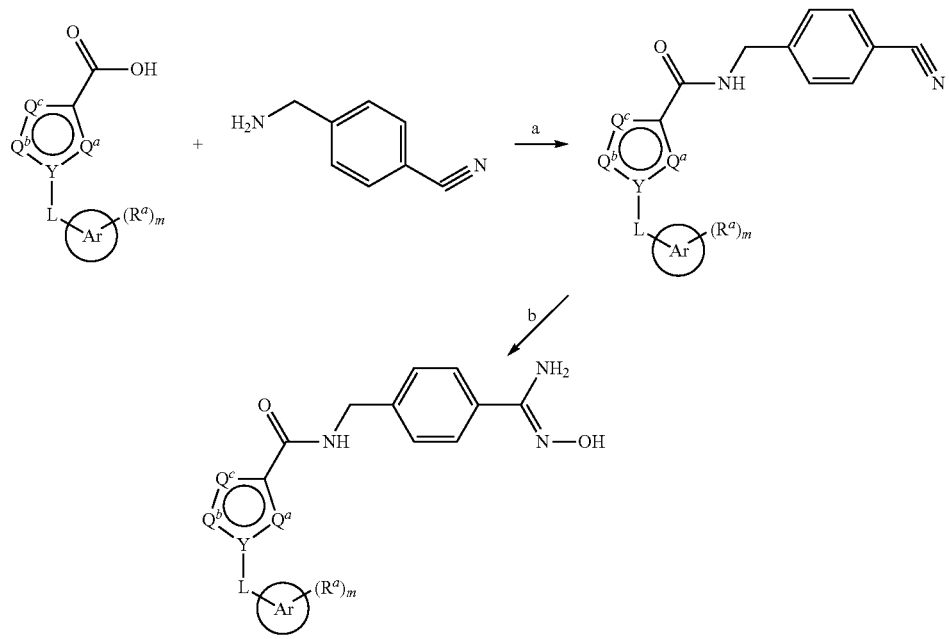

In step b, the product of the first reaction is reacted with hydroxylamine hydrochloride (3 equivalents) in ethanol at 80° C. for 3 h, and the final product obtained by solvent removal.

In the reaction described above, any reactive groups present on the compound of general formula I, such as hydroxyl, carboxy, amino, alkylamino or imino group may be protected during the reaction by conventional protecting groups well-known to skilled artisans, which can be subsequently removed by well-known chemical methods after the reaction is completed.

The preferred methods of synthesis of the compounds of the present invention, as described above, have an additional advantage in that such compounds (e.g., those of general formula I) may be synthesized in fewer steps than the corresponding PK inhibitors (e.g., those of general formula II), and thus provide industrial utility in reducing the cost and complexity of manufacture of PK inhibitor compounds for administration to a subject in need of treatment for a plasma kallikrein-dependent disease or condition.

V. Pharmaceutical Compositions

In addition to having compounds of formula I and III provided above, the compositions for prevention and treatment of plasma kallikrein-related diseases or conditions in humans and animals typically contain a pharmaceutical carrier, excipient and diluent.

The pharmaceutical compositions for the administration of the compounds of this invention may conveniently be presented in unit dosage form and may be prepared by any of the methods well known in the art of pharmacy and drug delivery. All methods include the step of bringing the active ingredient into association with the carrier, which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation.

In the pharmaceutical composition, the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions and self emulsifications as described in U.S. Patent Application No. 2002-0012680, hard or soft capsules, syrups, elixirs, solutions, buccal patch, oral gel, chewing gum, chewable tablets, effervescent powder and effervescent tablets. Compositions intended for oral use may be prepared according to any method known to the art for the manufacture of pharmaceutical compositions and such compositions may contain one or more agents selected from the group consisting of sweetening agents, flavoring agents, coloring agents, antioxidants and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as cellulose, silicon dioxide, aluminum oxide, calcium carbonate, sodium carbonate, glucose, mannitol, sorbitol, lactose, calcium phosphate or sodium phosphate; granulating and disintegrating agents, for example, corn starch, or alginic acid; binding agents, for example PVP, cellulose, PEG, starch, gelatin or acacia, and lubricating agents, for example magnesium stearate, stearic acid or talc. The tablets may be uncoated or they may be coated, enterically or otherwise, by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,166,452; and 4,265,874 to form osmotic therapeutic tablets for controlled release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Additionally, emulsions can be prepared with a non-water miscible ingredient such as oils and stabilized with surfactants such as mono-diglycerides, PEG esters and the like.

Aqueous suspensions contain the active materials in admixture with excipients suitable for the manufacture of aqueous suspensions. Such excipients are suspending agents, for example sodium carboxymethylcellulose, methylcellulose, oleagino-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example, arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. Oral solutions can be prepared in combination with, for example, cyclodextrin, PEG and surfactants.

The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols. Additionally, the compounds can be administered via ocular delivery by means of solutions or ointments. Still further, transdermal delivery of the subject compounds can be accomplished by means of iontophoretic patches and the like. For topical use, creams, ointments, jellies, solutions or suspensions, etc., containing the compounds of the present invention are employed. As used herein, topical application is also meant to include the use of mouth washes and gargles, as well as eye-drops for opthalmological use.

The compounds of the invention may be formulated for depositing into a medical device, which may include any of variety of conventional grafts, stents, including stent grafts, catheters, balloons, baskets or other device that can be deployed or permanently implanted within a body lumen. As a particular example, it would be desirable to have devices and methods which can deliver compounds of the invention to the region of a body which has been treated by interventional technique.

In exemplary embodiment, the inhibitory agent of this invention may be deposited within a medical device, such as a stent, and delivered to the treatment site for treatment of a portion of the body.

Stents have been used as delivery vehicles for therapeutic agents (i.e., drugs). Intravascular stents are generally permanently implanted in coronary or peripheral vessels. Stent designs include those of U.S. Pat. No. 4,733,655 (Palmaz), U.S. Pat. No. 4,800,882 (Gianturco), or U.S. Pat. No. 4,886,062 (Wiktor). Such designs include both metal and polymeric stents, as well as self-expanding and balloon-expandable stents. Stents may also used to deliver a drug at the site of contact with the vasculature, as disclosed in U.S. Pat. No. 5,102,417 (Palmaz) and in International Patent Application Nos. WO 91/12779 (Medtronic, Inc.) and WO 90/13332 (Cedars—Sanai Medical Center), U.S. Pat. No. 5,419,760 (Narciso, Jr.) and U.S. Pat. No. 5,429,634 (Narciso, Jr.), for example. Stents have also been used to deliver viruses to the wall of a lumen for gene delivery, as disclosed in U.S. patent application Ser. No. 08/746,404, filed Nov. 8, 1996 (Donovan et al.).

The term "deposited" means that the inhibitory agent is coated, adsorbed, placed, or otherwise incorporated into the device by methods known in the art. For example, the inhibitory agent may be embedded and released from within ("matrix type") or surrounded by and released through ("reservoir type") polymer materials that coat or span the medical device. In the later example, the inhibitory agent may be entrapped within the polymer materials or coupled to the polymer materials using one or more the techniques for generating such materials known in the art. In other formulations, the inhibitory agent may be linked to the surface of the medical device without the need for a coating by means of detachable bonds and release with time, can be removed by active mechanical or chemical processes, or are in a permanently immobilized form that presents the inhibitory agent at the implantation site.

In one embodiment, the inhibitory agent may be incorporated with polymer compositions during the formation of biocompatible coatings for medical devices, such as stents. The coatings produced from these components are typically homogeneous and are useful for coating a number of devices designed for implantation.

The polymer may be either a biostable or a bioabsorbable polymer depending on the desired rate of release or the desired degree of polymer stability, but a bioabsorbable polymer is preferred for this embodiment since, unlike a biostable polymer, it will not be present long after implantation to cause any adverse, chronic local response. Bioabsorbable polymers that could be used include, but are not limited to, poly(L-lactic acid), polycaprolactone, polyglycolide (PGA), poly (lactide-co-glycolide) (PLLA/PGA), poly(hydroxybutyrate), poly(hydroxybutyrate-co-valerate), polydioxanone, polyorthoester, polyanhydride, poly(glycolic acid), poly(D-lactic acid), poly(L-lactic acid), poly(D,L-lactic acid), poly(D,L-lactide) (PLA), poly(L-lactide) (PLLA), poly(glycolic acid-co-trimethylene carbonate) (PGA/PTMC), polyethylene oxide (PEO), polydioxanone (PDS), polyphosphoester, polyphosphoester urethane, poly(amino acids), cyanoacrylates, poly(trimethylene carbonate), poly(iminocarbonate), copoly (ether-esters) (e.g., PEO/PLA), polyalkylene oxalates, polyphosphazenes and biomolecules such as fibrin, fibrinogen, cellulose, starch, collagen and hyaluronic acid, polyepsilon caprolactone, polyhydroxy butyric acid, polyorthoesters, polyacetals, polydihydropyrans, polycyanoacrylates, cross linked or amphipathic block copolymers of hydrogels, and other suitable bioabsorbable poplymers known in the art. Also, biostable polymers with a relatively low chronic tissue response such as polyurethanes, silicones, and polyesters could be used and other polymers could also be used if they can be dissolved and cured or polymerized on the medical device such as polyolefins, polyisobutylene and ethylene-alphaolefin copolymers; acrylic polymers and copolymers, vinyl halide polymers and copolymers, such as polyvinyl chloride; polyvinylpyrrolidone; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; pyran copolymer; polyhydroxy-propyl-methacrylamide-phenol; polyhydroxyethyl-aspartamide-phenol; polyethyleneoxide-polylysine substituted with palmitoyl residues; polyamides, such as Nylon 66 and polycaprolactam; alkyd resins, polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Polymers and semipermeable polymer matrices may be formed into shaped articles, such as valves, stents, tubing, prostheses and the like.

In one embodiment of the invention, the inhibitory agent of the invention is coupled to a polymer or semipermeable polymer matrix that is formed as a stent or stent-graft device.

Typically, polymers are applied to the surface of an implantable device by spin coating, dipping or spraying. Additional methods known in the art can also be utilized for this purpose. Methods of spraying include traditional methods as well as microdeposition techniques with an inkjet type of dispenser. Additionally, a polymer can be deposited on an implantable device using photo-patterning to place the polymer on only specific portions of the device. This coating of the device provides a uniform layer around the device which allows for improved diffusion of various analytes through the device coating.

In preferred embodiments of the invention, the inhibitory agent is formulated for release from the polymer coating into the environment in which the medical device is placed. Preferably, the inhibitory agent is released in a controlled manner over an extended time frame (e.g., months) using at least one of several well-known techniques involving polymer carriers or layers to control elution. Some of these techniques were previously described in U.S. Patent Application 20040243225A1, the entire disclosure of which is incorporated in its entirety.

Moreover, as described for example in U.S. Pat. No. 6,770,729, which is incorporated herein in its entirety, the reagents and reaction conditions of the polymer compositions can be manipulated so that the release of the inhibitory agent from the polymer coating can be controlled. For example, the diffusion coefficient of the one or more polymer coatings can be modulated to control the release of the inhibitory agent from the polymer coating. In a variation on this theme, the diffusion coefficient of the one or more polymer coatings can be controlled to modulate the ability of an analyte that is present in the environment in which the medical device is placed (e.g. an analyte that facilitates the breakdown or hydrolysis of some portion of the polymer) to access one or more components within the polymer composition (and for example, thereby modulate the release of the inhibitory agent from the polymer coating). Yet another embodiment of the invention includes a device having a plurality of polymer coatings, each having a plurality of diffusion coefficients. In such embodiments of the invention, the release of the inhibitory agent from the polymer coating can be modulated by the plurality of polymer coatings.

In yet another embodiment of the invention, the release of the inhibitory agent from the polymer coating is controlled by modulating one or more of the properties of the polymer composition, such as the presence of one or more endogenous or exogenous compounds, or alternatively, the pH of the polymer composition. For example, certain polymer compositions can be designed to release an inhibitory agent in response to a decrease in the pH of the polymer composition. Alternatively, certain polymer compositions can be designed to release the inhibitory agent in response to the presence of hydrogen peroxide.

VI. PK-dependent Diseases or Conditions

Further to the introduction of PK-dependent diseases or conditions provided in the Background of the Invention, the importance of bradykinin in vasogenic edema is further illustrated in hereditary angioedema, in which individuals have little or no functional C1-Inhibitor, the major endogenous inhibitor of PK. High levels of bradykinin are generated in these individuals resulting in extravasation of fluid and protein from the plasma into soft tissue, thus causing life-threatening edema.

For example, bradykinin and its receptors have been shown to be involved in tumor angiogenesis (Ikeda, Y., et al. (2004)

Cancer Research 64: 5178-5185), pulmonary hypertension (Taraseviciene-Stewart, L., et al. (2005) Peptides 26: 1292-1300), and asthma (Barnes, P. J., (1992) Recent Progress on Kinins, AAS38/III, Birkhauser Verlag Basel).

C1-Inhibitor is also known to be involved in the pathogenesis of age-related macular degeneration (Ennis, S., et al. (2008) Lancet 372: 1828-1834) and ischemia-reperfusion injury following organ transplant or myocardial infarction (Inderbitzin, D., et al. (2004) Eur. Surg. Res. 36: 142-147; Horstick, G., et al. (2001) Circulation 104: 3125-3131).

For patients with angioedema conditions, a small polypeptide PK inhibitor (DX-88, ecallantide) alleviates edema in patients with HAE (Williams, A. et al. (2003) Transfus. Apher. Sci. 29: 255-258; Schneider, L. et al. (2007) J Allergy Clin Immunol. 120(2):416-22; Levy, J. H. et al. (2006) Expert Opin. Invest. Drugs 15: 1077-1090). Similarly, a bradykinin B2 receptor antagonist, icatibant, is also effective in treating HAE (Bork, K. et al. (2007) J. Allergy Clin. Immunol. 119: 1497-1503). In view of the role of PK in generating bradykinin, inhibition of PK can inhibit bradykinin production.

In related disorders, thrombogenesis results from fibrinolytic treatment (e.g. tissue plasminogen activator, streptokinase), and higher levels of PK are found in patients undergoing fibrinolysis (Hoffmeister, H. M. et al. (1998) J. Cardiovasc. Pharmacol. 31: 764-72). Plasmin-mediated activation of the intrinsic pathway has been shown to occur in plasma and blood and was markedly attenuated in plasma from individuals deficient in any of the intrinsic pathway components (Ewald, G. A. et al. (1995) Circulation 91: 28-36).

Individuals who have had an acute MI were found to have elevated levels of activated PK and thrombin (Hoffmeister, H. M., et al. (1998) Circulation 98: 2527-33).

DX-88 reduced brain edema, infarct volume and neurological deficits in an animal model of ischemic stroke (Storini, C., et al. (2006) J. Pharm. Exp. Ther. 318: 849-854). C1-INH reduced infarct size in a mouse model of middle cerebral artery occlusion (DeSimoni, M. G., et al. (2004) Am. J. Pathol. 164: 1857-1863; Akita, N., et al. (2003) Neurosurgery 52: 395-400). By way of correlation, the PK inhibitor ASP-440 was shown to reduce infarction volume and cerebrovascular edema in a rat model of ischemic stroke, and expansion of intracerebral hemorrhage in a model of hemorrhagic stroke (Methods for Treatment of Kallikrein-Related Disorders, WIPO, PCT WO 2009/0971; Liu, J., et al, Nat Med. (2011)17: 206-10). B2 receptor antagonists were found to reduce the infarct volume, brain swelling and neutrophil accumulation and were neuroprotective in an animal model of ischemic stroke (Zausinger, S., et al., (2003) Acta Neurochir. Suppl. 86: 205-207; Lumenta, D. B., et al. (2006) Brain Res. 1069: 227-234; Ding-Zhou, L., et al. (2003) Br. J. Pharmacol. 139: 1539-1547).

Regarding complications associated with cardiopulmonary bypass (CPB) surgery, it has been found that the contact system is activated during CPB (Wachtfogel, Y. T. (1989) Blood 73: 468) consequently resulting in up to a 20-fold increase in plasma bradykinin (Cugno, M. et al. (2006) Chest 120: 1776-1782; and Campbell, D. J. et al. (2001) Am. J. Physiol. Reg. Integr. Comp. Physiol. 281: 1059-1070). Capillary leak syndrome associated with CPB can be reduced using a PK inhibitor (Mojcik, C. F., Levy, J. H., Ann Thorac Surg. 2001 February; 71(2):745-54).

PK inhibitors, P8720 and PKSI-527 have also been found to reduce joint swelling in rat models of arthritis (see, De La Cadena, R. A. et al. (1995) FASEB J 9: 446-452; Fujimori, Y. (1993) Agents Action 39: 42-48). It has also been found that inflammation in animal models of arthritis was accompanied by activation of the contact system (Blais, C. Jr. et al. (1997) Arthritis Rheum. 40: 1327-1333).

The PK inhibitor P8720 has been found to reduce inflammation in an acute and chronic rat model of inflammatory bowel disease, IBD (Stadnicki, A. et al. (1998) FASEB J, 12(3):325-33; Stadnicki, A. et al. (1996) Dig. Dis. Sci. 41: 912-920; De La Cadena, R. A., et al. (1995) FASEB J. 9: 446-452). The contact system is activated during acute and chronic intestinal inflammation (Sartor, R. B. et al. (1996) Gastroenterology 110: 1467-1481). It has been found that a B2 receptor antagonist, an antibody to high molecular weight kininogen or reduction in levels of kininogen reduced clinicopathology in animal models of IBD (Sartor, R. B. et al. (1996) Gastroenterology 110: 1467-1481; Arai, Y. et al. (1999) Dig. Dis. Sci. 44: 845-851; Keith, J. C. et al. (2005) Arthritis Res. Therapy 7: R769-R776).

Still further, H-D-Pro-Phe-Arg-CMK, an inhibitor of PK and FXIIa, as well as C1-Inhibitor have been shown to reduce vascular permeability in multiple organs and reduce lesions in LPS or bacterial induced sepsis in animals (Liu, D. et al. (2005) Blood 105: 2350-2355; Persson, K. et al. (2000) J. Exp. Med. 192: 1415-1424). Clinical improvement was observed in sepsis patients treated with C1-Inhibitor (Zeerleder, S. et al. (2003) Clin. Diagnost. Lab. Immunol. 10: 529-535; Caliezi, C., et al. (2002) Grit. Care Med. 30: 1722-8; and Marx, G. et al. (1999) Intensive Care Med. 25: 1017-20). Fatal cases of septicemia are found to have a higher degree of contact activation (Martinez-Brotons, F. et al. (1987) Thromb. Haemost. 58: 709-713; Kalter, E. S. et al. (1985) J. Infect. Dis. 151: 1019-1027).

It has also been found that prePK levels are higher in diabetics, especially those with proliferative retinopathy, and correlate with fructosamine levels (Gao, B.-B., et al. (2007) Nature Med. 13: 181-188; Kedzierska, K. et al. (2005) Archives Med. Res. 36: 539-543). PrePK is also found to be elevated in diabetics and is highest in those with a sensomotor neuropathy (Christie, M. et al. (1984) Thromb. Haemostas. 52: 221-223). PK has been found to mediate hyperglycemia-induced cerebral hematoma expansion (Liu et al. (2011) Nat. Med. 17:206-210) in a model of hemorrhagic stroke, and to mediate retinal vascular dysfunction and induce retinal thickening in diabetic rats (Clermont et al. (2011) Diabetes, epub ahead of print March 28) in a model of diabetic retinopathy. PrePK levels are elevated in diabetics and are associated with increased blood pressure, independently correlate with the albumin excretion rate, and are elevated in diabetics with macroalbuminuria suggesting prePK may be a marker for progressive nephropathy (Jaffa, A. A. et al. (2003) Diabetes 52: 1215-1221). B1 receptor antagonists have been found to decrease enhanced vascular permeability and plasma leakage into various organs, including the skin and retina, in rats with streptozotocin-induced diabetes (Lawson, S. R. et al. (2005) Eur. J. Pharmacol. 514: 69-78; Lawson S R, Gabra B H, et al (2005) Regul Pept. 124:221-4). B1 receptor antagonists can also prevent streptozotocin-treated mice from developing hyperglycemia and renal dysfunction (Zuccollo, A., et al. (1996) Can. J Physiol. Pharmacol. 74: 586-589).

Therefore, diseases or conditions that can be treated using the compounds of the present invention include, but are not limited to, ischemic stroke, hemorrhagic stroke, hypertension and its vascular complications (especially retinopathy and nephropathy), cerebrovascular edema, pulmonary hypertension, inflammation, pain, acute myocardial infarction (MI), deep vein thrombosis (DVT), complications from fibrinolytic treatment (e.g., with tissue plasminogen activator, streptokinase) following stroke or MI, angina, angioedema, sepsis, arthritis, complications of cardiopulmonary bypass, capillary leak syndrome, inflammatory bowel disease, diabetes and its vascular complications (especially retinopathy, diabetic macular edema, nephropathy and neuropathy), age-related macular degeneration, retinal vein occlusions, brain edema, ischemia-reperfusion injury, angiogenesis (e.g., in cancer), asthma, anaphylaxis, and cerebrovascular complications of neurological conditions (e.g., Alzheimer's Disease, Parkinson's Disease, multiple sclerosis, CNS infections, and glioblastoma multiforme).

Upon administration to a subject in need thereof, the compounds of general formulae I and III of the present invention will be converted in vivo into PK inhibitors, and therefore lead to inhibition of both the intrinsic pathway of blood coagulation, as well as the formation of bradykinin from high molecular weight kininogen. In this regard, the compounds of the present invention have many pharmaceutical advantages over other PK inhibitors described in the art. One advantage is in that their administration to a subject via most clinically useful routes, e.g., oral, subcutaneous, topical (including opthalmological eye-drops), intraocular injection, etc., will result in higher levels of PK inhibitor compound in plasma or the disease-affected organ (e.g., the eye) when compared to administration of the corresponding PK inhibitor compound (described in WO 2008/016883, and U.S. Pat. No. 7,625,944) at a similar dose. This can result in a greater extent of inhibition of PK in vivo, and therefore a larger therapeutic effect. Another advantage is that their administration via routes such as subcutanedus, intramuscular or topical, will result in a slower appearance of the PK inhibitor compound in plasma or the disease-affected organ (e.g., the eye), thus effectively prolonging the time-period over which therapeutically useful levels of compound will be maintained in vivo. Thus, less frequent dosing would be required to maintain therepeutic levels in a subject in need of treatment with a PK inhibitor.

The following examples are provided to illustrate various aspects of the present invention.

EXAMPLE 1

Synthesis of 1-(4-fluorophenyl)-N-[[4-(N'-hydroxycarbamimidoyl)phenyl]methyl]-2,5-dimethyl-pyrrole-3-carboxamide

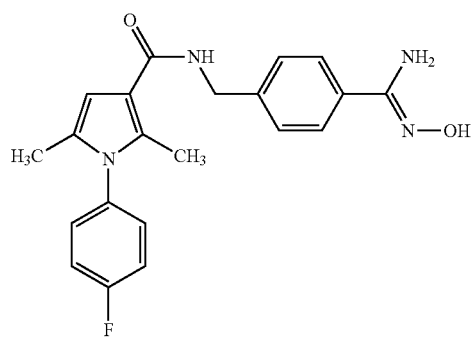 [SMILES: Cc1cc(C(=O)NCc2ccc(/C(N)=N/O)cc2)c(C)n1-c1ccc(F)cc1]

30 g of 1-(4-fluorophenyl)-2,5-dimethyl-pyrrole-3-carboxylic acid was reacted with 1 equivalent of 4-(aminomethyl)benzonitrile, in the presence of 1.1 equivalents of oxalyl chloride, 3 equivalents of triethylamine in dichloromethane at room temperature for 3 h. The product was then reacted with hydroxylamine hydrochloride (3 equivalents) in ethanol at 80° C. for 3 h. The target compound (36 g) was obtained as a tan-colored powder following solvent removal by evaporation. Purity assessed by HPLC was 97.8%, and mass was verified by LC/MS/MS (predicted m+1=381.2, obtained m+1=381.2). $^1$H-NMR (DMSO): δ 1.93 (3H), 2.21 (3H), 4.39-4.40 (2H), 5.76 (2H), 6.42 (1H), 7.26-7.28 (2H), 7.35-7.40 (4H), 7.60-7.62 (2H), 8.22 (1H), 9.56 (1H).

EXAMPLE 2

Conversion of prodrug 1-(4-fluorophenyl)-N-[[4-(N'-hydroxycarbamimidoyl)phenyl]methyl]-2,5-dimethyl-pyrrole-3-carboxamide in vivo into the active plasma kallikrein inhibitor N-[(4-carbamimidoylphenyl)methyl]-1-(4-fluorophenyl)-2,5-dimethyl-pyrrole-3-carboxamide Young male Sprague-Dawley rats were orally dosed at 25 mg/kg with the prodrug 1-(4-fluorophenyl)-N-[[4-(N'-hydroxycarbamimidoyl)phenyl]methyl]-2,5-dimethyl-pyrrole-3-carboxamide dissolved in PEG400. Blood was removed at various time intervals via an arterial catheter into a citrated collection tube, and plasma generated by centrifugation. The concentration of the active plasma kallikrein inhibitor N-[(4-carbamimidoylphenyl)methyl]-1-(4-fluorophenyl)-2,5-dimethyl-pyrrole-3-carboxamide in the plasma samples were determined using LC/MS/MS. The appearance of the active compound in plasma (see Table 1 below) demonstrated that the prodrug compound 1-(4-fluorophenyl)-N-[[4-(N'-hydroxycarbamimidoyl)phenyl]methyl]-2,5-dimethyl-pyrrole-3-carboxamide was absorbed from the gastrointestinal tract following oral dosing, and effectively converted in vivo into the active compound N-[(4-carbamimidoylphenyl)methyl]-1-(4-fluorophenyl)-2,5-dimethyl-pyrrole-3-carboxamide.

TABLE 1

| Time, h | N-[(4-carbamimidoylphenyl)methyl]-1-(4-fluorophenyl)-2,5-dimethyl-pyrrole-3 carboxamide plasma levels (ng/mL, mean ± s.d.) |
|---|---|
| 0.25 | 299 ± 128 |
| 0.5 | 380 ± 75 |
| 1 | 312 ± 102 |
| 2 | 168 ± 21 |
| 4 | 83 ± 15 |
| 8 | 43 ± 16 |
| 12 | 43 ± 27 |

EXAMPLE 3

Synthesis of 1-benzyl-N-[[4-(N'-hydroxycarbamimidoyl)phenyl]methyl]pyrazole-4-carboxamide

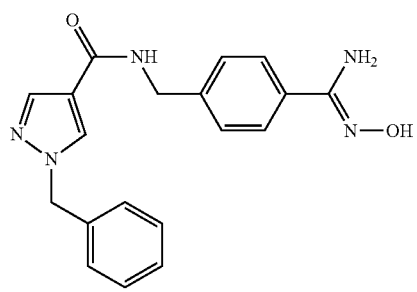 [SMILES: N/C(=N\O)c1ccc(CNC(=O)c2cnn(Cc3ccccc3)c2)cc1]

20.8 g of 1-benzylpyrazole-4-carboxylic acid was reacted with 1 equivalent of 4-(aminomethyl)benzonitrile, in the presence of 1.1 equivalents of oxalyl chloride, 3 equivalents of triethylamine in dichloromethane at room temperature for 3 h. The product was then reacted with hydroxylamine hydrochloride (3 equivalents) in ethanol at 80° C. for 3 h. The target compound (17.5 g) was obtained as a off-white powder following solvent removal by evaporation. Purity assessed by HPLC was 98.7%, and mass was verified by LC/MS/MS (predicted m+1=350.2, obtained m+1=350.2). $^1$H-NMR (DMSO): δ 4.39-4.40 (2H), 5.34 (2H), 5.76 (2H), 7.25-7.30 (4H), 7.34-7.36 (3H), 7.59-7.62 (2H), 7.91 (1H), 8.27 (1H), 8.63 (1H), 9.57 (1H).

What is claimed is:

1. A compound having the formula:

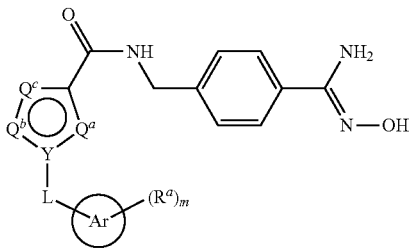

(I)

or a pharmaceutically acceptable salt thereof, wherein

Ar is an aromatic ring selected from the group consisting of benzene, pyridine and pyrimidine;

m is an integer from 0-5;

each $R^a$ is independently selected from the group consisting of cycloalkyl, haloalkyl, halogen, —OH, —OR$^1$, —OSi(R$^1$)$_3$, —OC(O)O—R$^1$, —OC(O)R$^1$, —OC(O)NHR$^1$, —OC(O)N(R$^1$)$_2$, —SH, —SR$^1$, —S(O)R$^1$, —S(O)$_2$R$^1$, —SO$_2$NH$_2$, —S(O)$_2$NHR$^1$, —S(O)$_2$N(R$^1$)$_2$, —NHS(O)$_2$R$^1$, —NR$^1$S(O)$_2$R$^1$, —C(O)NH$_2$, —C(O)NHR$^1$, —C(O)N(R$^1$)$_2$, —C(O)R$^1$, —C(O)H, —C(=S)R$^1$, —NHC(O)R$^1$, —NR$^1$C(O)R$^1$, —NHC(O)NH$_2$, —NR$^1$C(O)NH$_2$, —NR$^1$C(O)NHR$^1$, —NHC(O) NHR$^1$, —NR$^1$C(O)N(R$^1$)$_2$, —NHC(O)N(R$^1$)$_2$, —CO$_2$H, —CO$_2$R$^1$, —NHCO$_2$R$^1$, —NR$^1$CO$_2$R$^1$, —R$^1$, —CN, —NO$_2$, —NH$_2$, —NHR$^1$, —N(R$^1$)$_2$, —NR$^1$S(O)NH$_2$, —NR$^1$S(O)$_2$NHR$^1$, —NH$_2$C (=NR$^1$)NH$_2$, —N=C(NH$_2$)NH$_2$, —C(=NR$^1$)NH$_2$, —NH—OH, —NR$^1$—OH, —NR$^1$—OR$^1$, —N=C=O, —N=C=S, —Si(R$^1$)$_3$, —NH—NHR$^1$, —NHC(O)NHNH$_2$, NO, —N=C=NR$^1$ and —S—CN, wherein each R$^1$ is independently alkyl or aryl;

L is a linking group selected from the group consisting of a bond, CH$_2$ and SO$_2$;

Q$^a$, Q$^b$, and Q$^c$ are each members independently selected from the group consisting of N, S, O and C(R$^q$) wherein each R$^q$ is independently selected from the group consisting of H, C$_{1-8}$ alkyl, halogen and phenyl; and Y is C or N; and the ring having Q$^a$, Q$^b$, Q$^c$ and Y as ring vertices is a five-membered ring having two double bonds.

2. The compound of claim 1, wherein Q$^a$ is N; and Q$^b$ and Q$^c$ are each selected from N, O and C(R$^q$).

3. The compound of claim 1, wherein Q$^a$ is N and Q$^b$ and Q$^c$ are each selected from N and C(R$^q$).

4. The compound of claim 1, wherein Y is N, and Q$^a$, Q$^b$ and Q$^c$ are each independently C(R$^q$), wherein each R$^q$ is independently H or C$_{1-8}$ alkyl.

5. The compound of claim 1, wherein Y is N, Q$^a$ and Q$^c$ are C(R$^q$) and Q$^b$ is CH.

6. The compound of claim 1, wherein Y is N and Q$^b$ is N.

7. The compound of claim 1, wherein L is a bond and Y is N.

8. The compound of claim 1, wherein L is a bond, Y is N, and Ar is a benzene ring.

9. The compound of claim 1, wherein L is a bond.

10. The compound of claim 1, wherein L is —SO$_2$—.

11. The compound of claim 1, wherein R$^a$ is H or C$_1$-C$_8$ alkyl.

12. The compound of claim 1, wherein Q$^a$ is O; and Q$^b$ and Q$^c$ are each selected from N, O and C(R$^q$).

13. The compound of claim 1, wherein Q$^a$ is O; and Q$^b$ and Q$^c$ are each selected from N and C(R$^q$).

14. The compound of claim 1, having the formula:

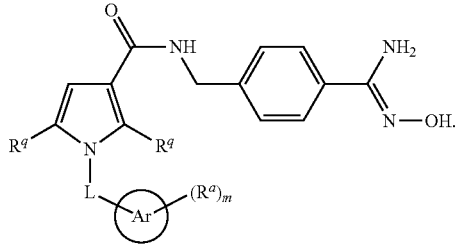

(Ia)

15. The compound of claim 14, wherein each R$^q$ is independently selected from the group consisting of H and C$_1$-C$_8$ alkyl; and L is a bond or —CH$_2$—.

16. The compound of claim 14, wherein L is a bond, Ar is benzene and R$^a$ is a halogen.

17. The compound of claim 14, wherein R$^a$ is —CF$_3$ or —CH$_2$CF$_3$.

18. The compound of claim 1, having the formula:

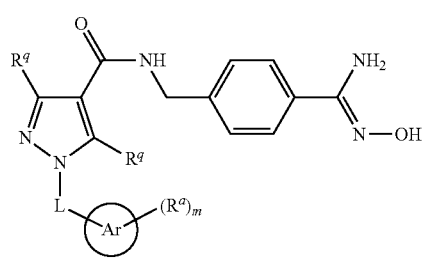

(Ib)

wherein Ar is an aromatic ring.

19. The compound of claim 18, wherein each R$^q$ is independently selected from the group consisting of H, halogen and C$_1$-C$_8$ alkyl.

20. The compound of claim 18, wherein L is selected from the group consisting of a bond and —CH$_2$—.

21. The compound of claim 18, wherein Ar is a benzene ring.

22. The compound of claim 18, wherein Ar is a benzene ring, m is 0, each R$^q$ is H, and L is —CH$_2$.

23. The compound of claim 1, selected from the group consisting of:
(a) 1-(4-fluorophenyl)-N-[[4-(N'-hydroxycarbamimidoyl) phenyl]methyl]-2,5-dimethyl-pyrrole-3-carboxamide;
(b) 1-(4-chlorophenyl)-N-[[4-(N'-hydroxycarbamimidoyl)phenyl]methyl]-2,5-dimethyl-pyrrole-3-carboxamide;

(c) 1-(4-methoxyphenyl)-N-[[4-(N'-hydroxycarbamimidoyl)phenyl]methyl]-2,5-dimethyl-pyrrole-3-carboxamide;
(d) 1-benzyl-N-[[4-(N'-hydroxycarbamimidoyl)phenyl]methyl]pyrazole-4-carboxamide;
(e) N-[[4-(N'-hydroxycarbamimidoyl)phenyl]methyl]-2,5-dimethyl-1-(4-pyridylmethyl)pyrrole-3-carboxamide.

24. A compound of claim 23, wherein said compound is 1-(4-fluorophenyl)-N-[[4-(N-hydroxycarbamimidoyl)phenyl]methyl]-2,5-dimethyl-pyrrole-3-carboxamide.

25. A compound of claim 23, wherein said compound is 1-benzyl-N-[[4-(N'-hydroxycarbamimidoyl)phenyl]methyl]pyrazole-4-carboxamide.

26. A method of treating a disease or condition selected from the group consisting of diabetic retinopathy and diabetic macular edema, said method comprising administering to a subject in need thereof a pharmaceutically effective amount of a compound of claim 1.

27. A method of claim 26, wherein said disease or condition is diabetic retinopathy.

28. A method of claim 26, wherein said disease or condition is diabetic macular edema.

29. A composition comprising a pharmaceutically acceptable excipient and a compound of claim 1.

30. A composition of claim 29, wherein said compound is selected from the group consisting of:
(a) 1-(4-fluorophenyl)-N-[[4-(N'-hydroxycarbamimidoyl)phenyl]methyl]-2,5-dimethyl-pyrrole-3-carboxamide;
(b) 1-(4-chlorophenyl)-N-[[4-(N'-hydroxycarbamimidoyl)phenyl]methyl]-2,5-dimethyl-pyrrole-3-carboxamide;
(c) 1-(4-methoxyphenyl)-N-[[4-(N'-hydroxycarbamimidoyl)phenyl]methyl]-2,5-dimethyl-pyrrole-3-carboxamide;
(d) 1-benzyl-N-[[4-(N'-hydroxycarbamimidoyl)phenyl]methyl]pyrazole-4-carboxamide;
(e) N-[[4-(N'-hydroxycarbamimidoyl)phenyl]methyl]-2,5-dimethyl-1-(4-pyridylmethyl)pyrrole-3-carboxamide.

31. A composition of claim 29, wherein said compound is 1-benzyl-N-[[4-(N'-hydroxycarbamimidoyl)phenyl]methyl]pyrazole-4-carboxamide.

* * * * *